United States Patent
Friedman

(10) Patent No.: US 6,616,448 B2
(45) Date of Patent: *Sep. 9, 2003

(54) DISPENSER FOR HEATING AND EXTRUDING DENTAL MATERIAL

(76) Inventor: Joshua Friedman, P.O. Box 2867, Danbury, CT (US) 06813

( * ) Notice: Subject to any disclaimer, the term of this patent is extended or adjusted under 35 U.S.C. 154(b) by 0 days.

This patent is subject to a terminal disclaimer.

(21) Appl. No.: 09/944,754

(22) Filed: Sep. 1, 2001

(65) Prior Publication Data

US 2002/0058231 A1 May 16, 2002

Related U.S. Application Data

(63) Continuation-in-part of application No. 09/667,851, filed on Sep. 22, 2000, now Pat. No. 6,312,254.

(51) Int. Cl.[7] .................................................. A61C 3/00
(52) U.S. Cl. ........................................... 433/32; 433/90
(58) Field of Search .............................. 433/32, 80, 89, 433/90; 222/146.2, 146.5, 390, 333

(56) References Cited

U.S. PATENT DOCUMENTS

| | | | |
|---|---|---|---|
| 4,684,344 A | 8/1987 | Brockway et al. | 433/81 |
| 5,026,187 A | * 6/1991 | Belanger et al. | 401/1 |
| 5,269,762 A | * 12/1993 | Armbruster et al. | 604/155 |
| 6,056,165 A | * 5/2000 | Speranza | 222/333 |

FOREIGN PATENT DOCUMENTS

DE          295 15 040          3/1997

* cited by examiner

Primary Examiner—Kevin Shaver
Assistant Examiner—Melba Bumgarner

(57) ABSTRACT

A dispenser for controllably heating a compule of dental material removably inserted in the dispenser and for extruding dental material from the compule. The dispenser includes an elongated tubular barrel having a substantially semi-cylindrical front end to accommodate the body of the compule, a cavity at the front end of the dispenser open to the atmosphere and a slot disposed transverse to the longitudinal axis of the for accommodating an end flange of the compule when the compule is inserted into the dispenser. The dispenser further includes a plunger reciprocally mounted in the tubular barrel in alignment with the longitudinal axis of the cavity for engaging the compule to express dental material from said compule by means of a motorized assembly or manual control under the control of the operator and a heating unit disposed in the cavity at the front end of the dispenser for heating the compule.

12 Claims, 8 Drawing Sheets

DISPENSER FOR HEATING AND EXTRUDING DENTAL MATERIAL

This invention is a continuation-in-part of application Ser. No. 09/667,851 filed Sep. 22, 2000, now U.S. Pat. No. 6,312,254 and relates to a dispenser for heating dental material in a compule and for controllably extruding the heated dental material from the dispenser prior to clinical application.

FIELD OF THE INVENTION

BACKGROUND OF INVENTION

In applicants co-pending patent application Ser. No. 09/020,107, the disclosure of which is herein incorporated by reference, a method is disclosed for preheating dental composite material within a container before extruding the material from the container into an oral cavity for clinical application. The dental composite material is preheated to an elevated temperature above that of ambient temperature just prior to placement into a prepared tooth in the oral cavity. The prepared tooth is then clinically treated by exposure to light radiation while the dental restorative composite material is at the elevated temperature. Conversely, at present, photocurable dental materials are extruded into the patients mouth at ambient temperature from a standard dispensing device and cured by exposure to light radiation at ambient temperature.

In accordance with the findings of the applicant and as taught in the aforementioned patent the physical properties of photocurable dental material(s) are enhanced when preheated just prior to clinical usage. Examples of dental materials which can be enhanced by preheating prior to use include restorative materials (commonly referred to as filling materials), etching agents, bleaching compositions, dental cements, impression materials and more particularly photocurable dental restorative materials.

Applicants application also teaches preheating one or more standard pre-filled computes of dental material using a small heating device capable of housing a plurality of pre-filled computes in a removable section of the device. The removable section acts as a heat sink for all of the computes permitting the removable section to be removed after being heated to an elevated temperature and placed close to the patient, preferably upon a standard bracket tray which most dentists presently use to hold instruments and medicaments, during a given operative procedure. Prior to use a heated compule is placed in a conventional dispenser by the dentist and dental material is then extruded directly into the prepared dental cavity.

Conventional dispensers are mechanical extruding devices such as is taught in U.S. Pat. No. 4,383,853 by Welsh and U.S. Pat. No. 5,489,207 by Dragon and have no other purpose. The dispenser of the present invention is a hand held portable device designed to heat a compule of dental material which is removably inserted in the dispenser to an elevated temperature above that of ambient and to controllably extrude the pre-heated dental material from the compule directly from the dispenser into an oral cavity for clinical application.

SUMMARY OF THE INVENTION

The present invention is directed to a dispenser for controllably heating a compule of dental material which is removably inserted into the dispenser and for extruding dental material from the compule. The compule has a circumferential flange at one end which surrounds a movable sealing plug and has a generally cylindrical body in which the dental material to be extruded is stored. The dispenser of the present invention comprises:

- an elongated section having a front end and a rear end with said front end having a cavity adapted for the removable placement of said compule,
- a plunger mounted for reciprocal movement within the elongated section of said dispenser in alignment with the cavity,
- means in response to the control of an operator for advancing the plunger into engagement with said compule to express dental material from said compule;
- a heating unit having a heating element located in the front end of said dispenser for heating substantially the entire compule in said cavity such that all or substantially all of the material in the compule is heated at one time;
- a supply of electrical energy and
- means for controlling the supply of electrical energy to said heating element in the heating unit. The means connected to the plunger can be a manually movable lever arm having one end connected to the plunger for controllably advancing the plunger into engagement with the compule to dispense dental material from the dispenser or a motorized control unit for automatically dispensing material in response to a command control signal from the operator. The motorized unit preferably including a lead screw and a gear box reducer to increase the output torque of the motor. For the embodiment in which the plunger is operated manually the movable lever should be spaced apart from the handle so that the lever and handle can be held in one hand by the operator of the dispenser and squeezed for controllably advancing the plunger as the lever moves relative to the handle. In the manually operated plunger embodiment the movable lever arm is preferably connected to the plunger by means of a rack and pinion mechanism.

BRIEF DESCRIPTION OF THE DRAWINGS

The features and advantages of the dispenser of the invention will become apparent from the following detailed description when read in conjunction with the accompanying drawings of which:

FIG. 4(a) is an enlarged fragmentary view in cross section of the front end of the dispenser of FIG. 4;

FIG. 5(a) is a view of the interior of the heating unit showing the heating element and thermocouple;

DETAILED DESCRIPTION OF THE PREFERRED EMBODIMENT

Figure 1:
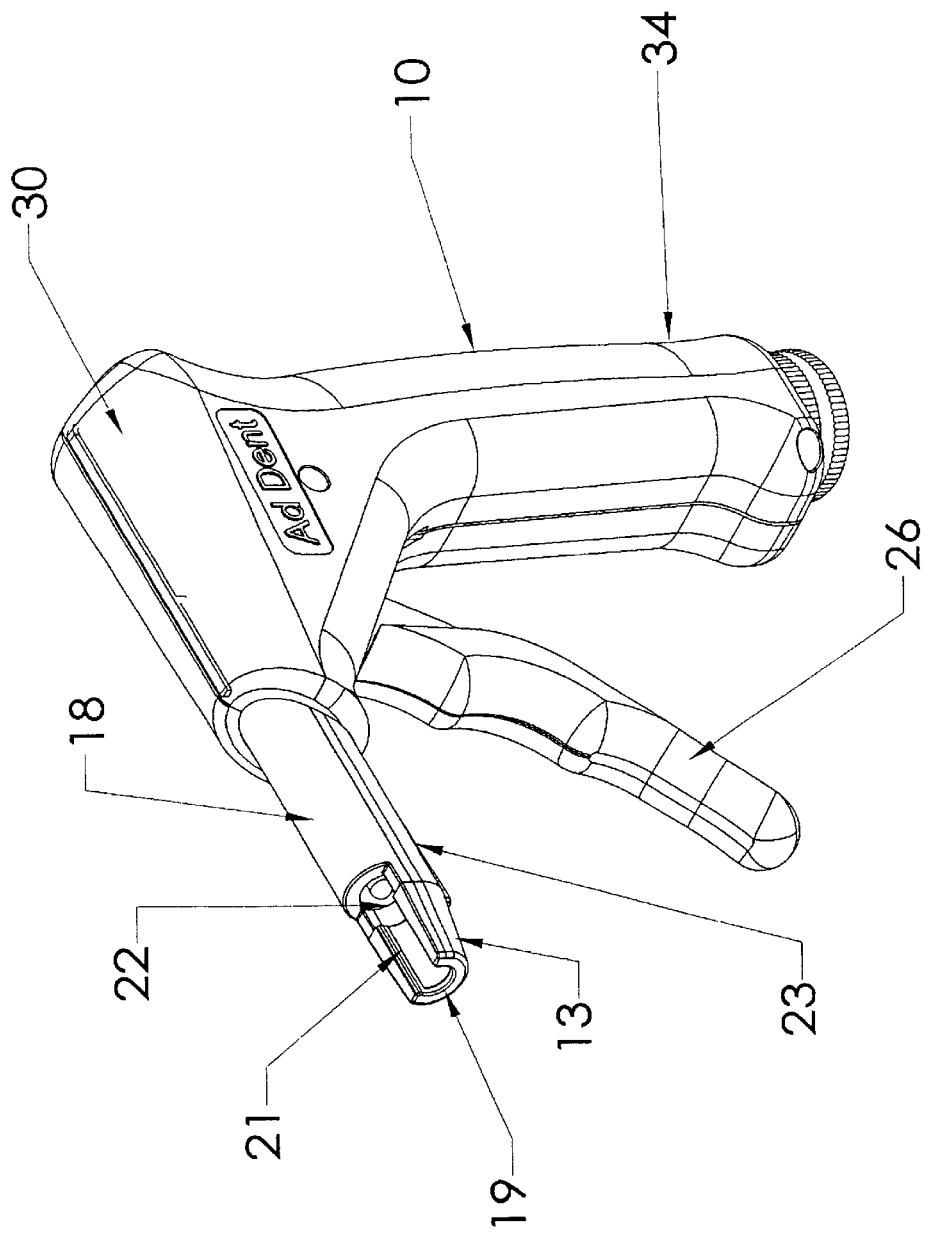
FIG. 1 is a perspective view of the manually operated dispenser of the present invention.
Figure 2:
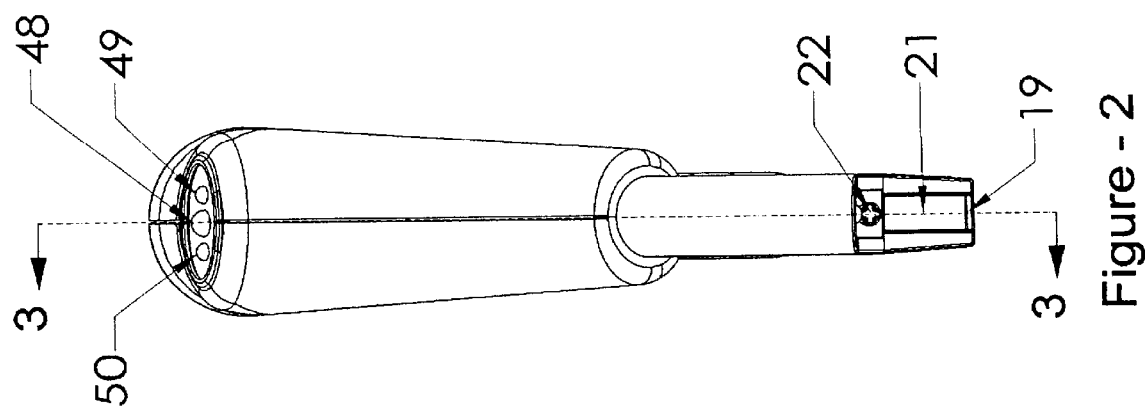
FIG. 2 is a top view of the dispenser shown in FIG. 1.

Referring to the drawings, and more particularly to FIGS. 1–4, there is shown a manual dispenser 10 for heating dental material stored in a disposable compule 12 and for controllably extruding the dental material from the compule 12. The disposable compule 12 is removably mounted in a compule holder 13 formed at the front end of the dispenser 10. The compule 12 may be any standard size commercially available cartridge in which dental material 14 is stored. The compule 12 is removably inserted into the dispenser 10 and may be manually ejected from the dispenser 10 for replacement after the photocurable dental material 14 has been emptied from the compule 12 as will be more fully discussed hereafter. A standard compule 12, as is presently commercially available, has a generally cylindrically shaped body 11 with an outer circumferential flange 9 at the rear end thereof with a diameter larger than the diameter of the body 11 and a nozzle tip 15 at its forward end having a discharge orifice 16 through which the dental material is discharged. The nozzle tip 15 may lie at any desired angle relative to the body 11. A movable sealing plug 17 holds the dental material 14 secure in the body 11 of the compule 12.

The dispenser 10 comprises a tubular barrel 18 having a semi-cylindrical shaped open front end 19 and a cavity 21 forming, in combination, a compule holder 13 into which the compule 12 is removably inserted. The tubular barrel 18 has a bore 20 extending longitudinally therethrough in coaxial alignment with a cavity 21 at the front end 19 of the dispenser 10. The cavity 21 is dimensioned to accommodate the generally cylindrical body 11 of the compule 12. A slot 22 is formed in the walls 23 of the open front end 19 of the dispenser 10 lying transverse to the longitudinal axis of the cavity 21 abutting the tubular barrel 18. The slot 22 is dimensioned to accommodate the flanged end 9 of the compule 12.

A plunger 24 is controllably reciprocated within the bore 20 of the tubular barrel 18 by means of a direct drive gear coupling 25 between the plunger 24 and a manually movable lever arm 26 in a configuration commonly referred to as a rack and pinion drive mechanism. The direct drive gear coupling 25 includes a rack represented by a first set of gear teeth 27 substantially at the rear end of the plunger 24 interconnected to a pinion represented by a second set of gear teeth 28 formed at one end of the manually movable lever arm 26. The manually movable lever arm 26 is pivotally connected through a pivot pin 29 secured to the casing 30 of the dispenser 10 which partially surrounds the barrel 18 as shown in FIG. 1. The plunger 24 has a piston 32 at the forward end thereof, as more clearly shown in FIG. 4, which is in coaxial alignment with the longitudinal axis of the cavity 21 and in alignment with the sealing plug 17 of the compule 12 when the compule 12 is inserted into the dispenser 10. The piston 32 moves the movable sealing plug 17 within the compule 12 as the plunger 24 is advanced by manually squeezing the lever arm 26.

Figure 6:
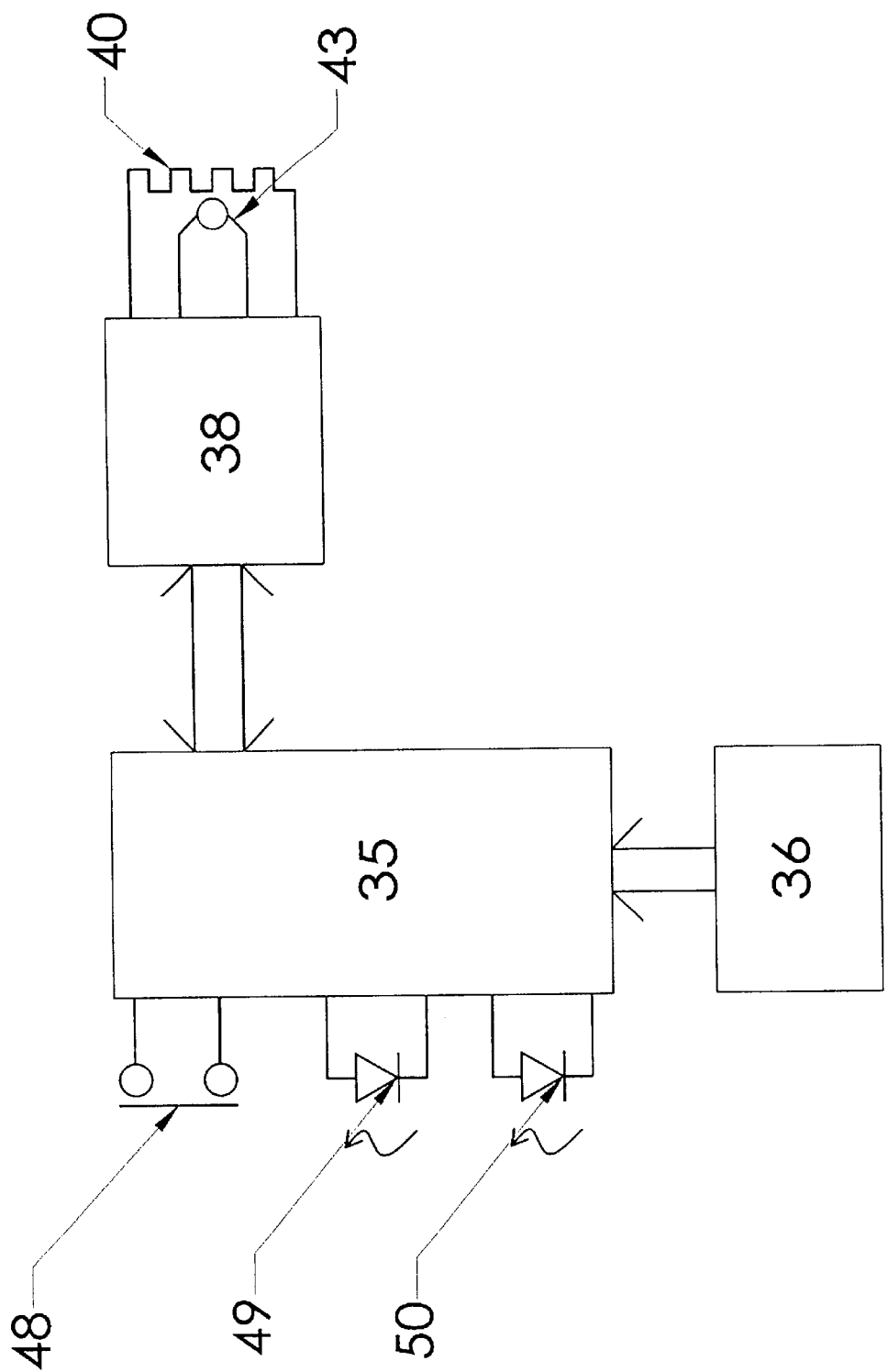
FIG. 6 is a block diagram of the heating control unit for controlling the temperature of the heating unit in FIG. 5.

The tubular barrel 18 is connected to a housing 30 containing an electrical control unit 35 which is shown in block diagram in FIG. 6. The housing 30 has a hollow tubular section 34 forming a handle for the dispenser 10 in the shape of a pistol grip. A battery or battery pack 36 which functions as a source of electrical power for heating the compule 12 is stored in the tubular section 34. The tubular section 34 of the housing 30 and the lever arm 26 are normally spaced apart such that the lever arm 26 and tubular section 34 can be conveniently held in one hand by an operator of the dispenser 10 and squeezed to move the lever arm 26 relative to the tubular section 34. A coiled tension spring 37 is connected to the movable lever arm 26 and to the housing 30 to maintain the lever arm 26 in a normally retracted position spaced apart from the tubular section 34 until the lever arm 26 is squeezed. Upon release of the movable lever arm 26 the coiled tension spring 37 forces the lever arm 26 back to its normal retracted position. In operation, the operator squeezes the movable lever arm 26 relative to the tubular section 34 which causes the plunger 24 to move forwardly pushing the piston 32 against the sealing plug 17 which, in turn, discharges dental material 14 from the dispenser 10. The amount of dental material 14 being discharged is proportional to the applied squeezing force on the movable lever arm 26. Once the operator releases the grip on the movable lever arm 26 the coiled tension spring 36 moves the movable lever arm 26 away from the tubular section 34 retracting the plunger 24. In the normal or unsqueezed position the plunger 24 is fully retracted and the lever arm 26 is spaced apart from the tubular section 34.

Figure 5:
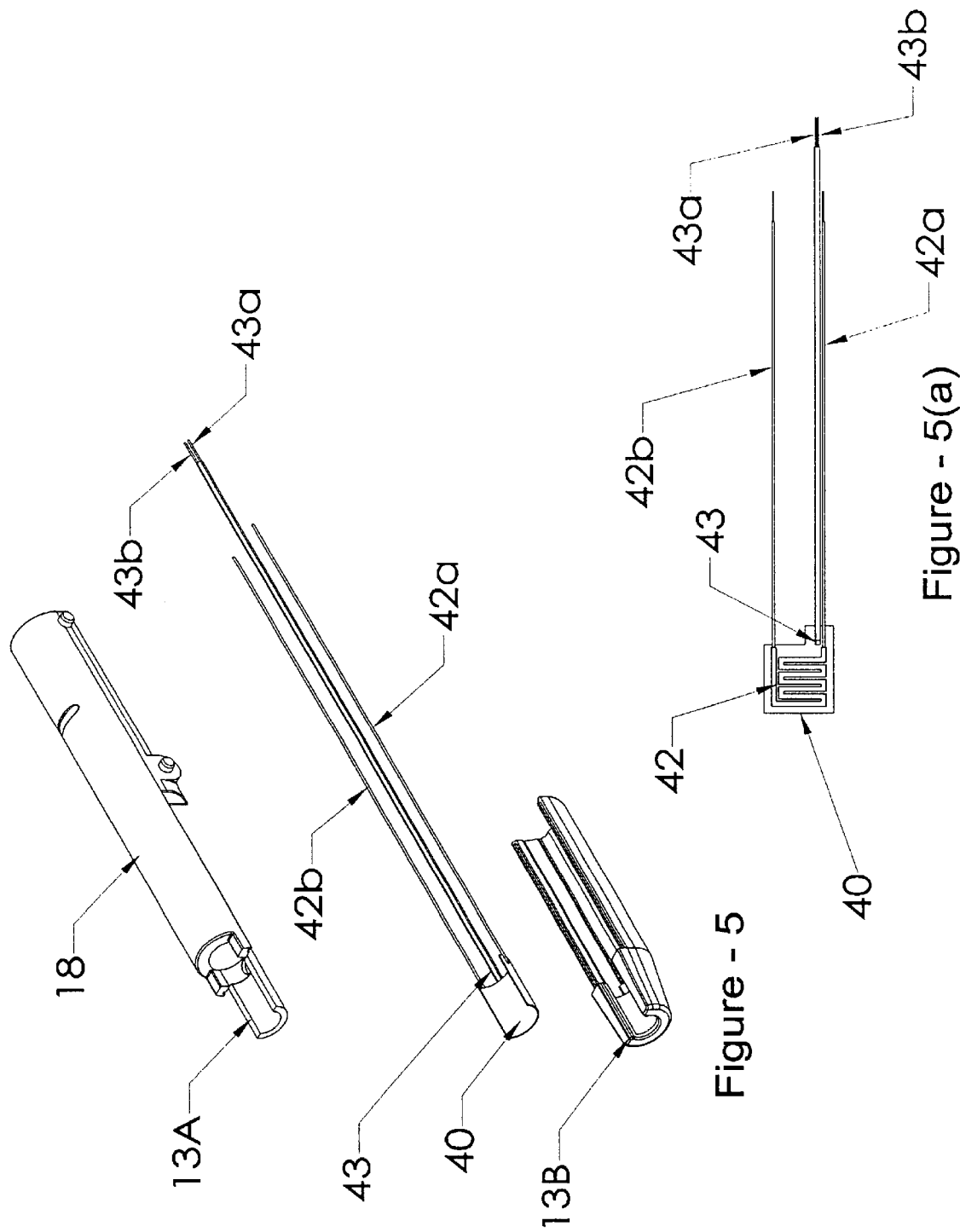
FIG. 5 is an exploded elevational view of a preferred embodiment for the front end of the dispenser shown in FIGS. 2 and 3.

A preferred embodiment of the front end of the dispenser 10 is shown in elevation in FIGS. 5 and 5(a) wherein the compule 12 has a first compule holder portion 13A extending from the tubular barrel 18 and a second compule holder portion 13B into which the first compule holder portion 13A slides after insertion of a heating unit 40 for raising the temperature of the compule 12 when mounted in the compule holder 13. The heating unit 40 is in the form of a flexible sheet of material which can be flexed into a desired shape to form a liner which covers the internal surface of the cavity 21 of the compule holder 13 into which the compule 12 is mounted. The heating unit 40 may be secured between the first compule holder portion 13A and the second compule holder portion 13B by means of an adhesive or any other conventional means. Alternatively, the heating unit 40 may be lined over the cavity 21 of the compule holder 13 or molded into the compule holder 13 to form an integral component thereof. The heating unit 40 includes a heating element 42 of a highly conductive material composed preferably of a metal such as copper, nichrome, aluminum or graphite in the form of a wire strip embedded in a plastic covering such as polyester. In addition the heating unit 40 includes a temperature sensor such as a conventional type J thermocouple 43. The wire strip heating element 42 is arranged in a pattern having a serpentine or interlaced geometry as shown in FIG. 5(a) and as disclosed in applicants patent application Ser. No. 09/020,107 the disclosure of which is herein incorporated by reference. The opposite ends of the wire strip heating element 42 in the heating unit 40 is connected to a set of electrical wires 42a and 42b which extend from the heating unit 40 through slots in the bore 20 of the tubular barrel 18 to the control unit 35 in a series circuit relationship. The thermocouple 43 in the heating unit 40 senses the temperature of the heating element 42 directly in the compule holder 13. Two wires 43a and 43b extend from the thermocouple 43 as shown in FIG. 5(a) which also extend from the heating unit 40 through slots in the bore 20 of the tubular barrel 18 to a heater drive 38 shown in FIG. 6.

The control unit 35, which preferably consists of a microprocessor (not shown), operates in conjunction with a source of electrical power such as the battery or battery pack 36 and the heater drive 38 to form a control system as shown in the block diagram of FIG. 6 for regulating the temperature of the heating element 42 in the heating unit 40. The battery pack 36 may consist of a group of rechargeable cells with any voltage between from 2.5 to 12 volts, preferably 3.6 volts and a capacity of at least 1.0 Ah. The battery pack 36 is the sole power source for the dispenser.

The heater drive 38 measures the resistance of the thermocouple 43. The control unit 35 regulates the electrical power supplied from the battery 36 to the heating unit 40 and as such regulates the temperature of the heating unit 40. The change in resistance of the thermocouple 43 is sensed by the microprocessor in the control unit 35 which adjusts the driving current of the power supply preferably by modification of the pulse width of the driving current in a relationship corresponding to changes in temperature. For example, if the temperature of the compule 12 goes up the resistance of the thermocouple goes down causing the microprocessor to shorten the pulse width of the driving current to the heating unit 40 which in turn eventually causes the temperature of the compule to drop. Conversely when the temperature of the compule 12 drops the resistance of the thermocouple rises to lengthen the pulse width etc. By regulating the pulse width of the driving current the temperature of the compule 12 is maintained at a predetermined level based upon the factory temperature setting of the thermocouple which for dispensing dental materials from the dispenser 10 should optimally be set between 130° F. to 140° F. But this temperature can be varied between 125° F. and 185° F., depending on the material and application.

The control unit 35 also provides an operator interface and operates all control functions. The operator interface consists of one pushbutton 48 and two LED's 49 and 50. The pushbutton power switch 48 will turn the dispenser on and off. The LED power indicator 49 will light when power is on and will blink when the battery pack voltage drops below 3.0V (in the case of a 3.6 volt battery). The LED 50 is a temperature indicator which will light when the desired temperature is reached. Pressing the power button 48 activates the control unit 35 which turns on the power LED 49 and heats up the heating unit 40. When the heating unit 40 attains the desired temperature the heater drive 38 will send a signal to the to the Control unit 35 which is programmed to wait 2 seconds and turn on the LED 50. The temperature of the heating unit 40 will continue to be regulated for a programmed period of 5 minutes unless during the 5 minute interval the power button 48 is again depressed. Depressing the power button 48 a second time, i.e., after it is turned on deactivates the control unit 35. The control unit 35 will also disable the supply of electrical power to the heating unit 40, when the microprocessor detects a low battery condition (e.g. a battery voltage of <3.0 volts) and cause the power LED 49 to blink during that time.

Figure 4:
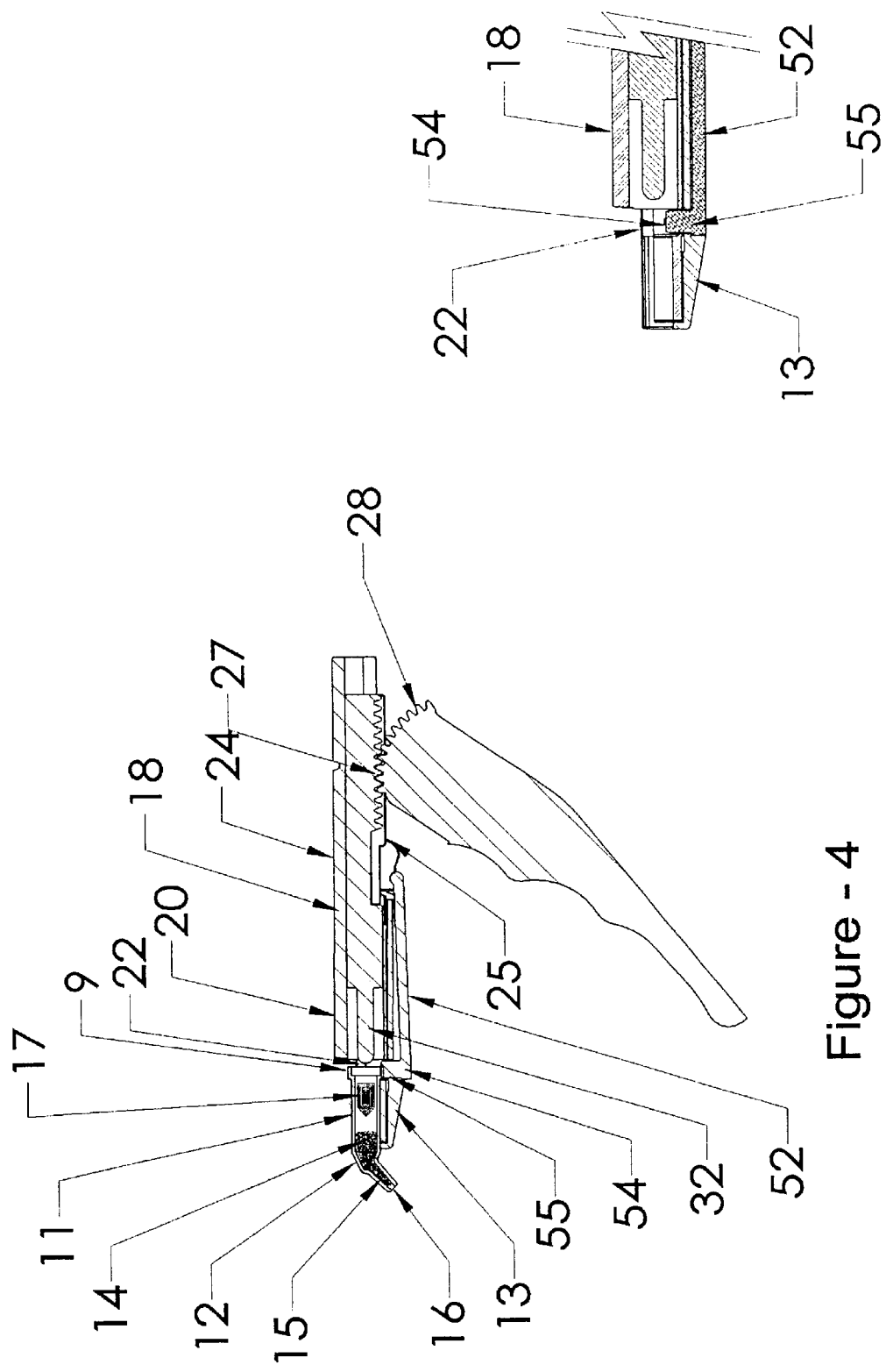
FIG. 4 is an enlarged cross sectional schematic of the front end of the dispenser, the plunger in the dispenser and the interconnected gearing for controlling the extrusion of dental material in accordance with the present invention.

The compule holder 13 at the front end 19 of the dispenser 10 has an ejector mechanism 51 including a compule ejector arm 52 which is pivotally connected to the tubular body 18 and extends into the compule holder 13 to permit the operator to quickly and easily remove the compule 12 from the compule holder 13. The ejector arm 52 has a head 54 extending into the slot 22 through an opening 55 in the underside of the compule holder 13 adjacent the flanged end 9 of the compule 12. The ejector arm 52 lies at an inclined angle relative to the longitudinal axis of the bore 20 in the tubular body 18 to provide additional mechanical advantage for moving the compule ejector arm 52. As shown in FIG. 4(a) when the compule 12 is to be removed from the compule holder 13 the ejector arm 52 is manually depressed causing the head 54 to push the flanged end 9 of the compule 12 upwardly out from the slot 22. In this position the operator can readily grip the compule 12 and remove it for replacement. With no compule 12 in place the ejector arm 52 remains flush with the body 18. The replacement of the compule 12 in the compule holder 13 repositions the ejector arm 52 as more clearly shown in FIG. 4.

Figure 3:
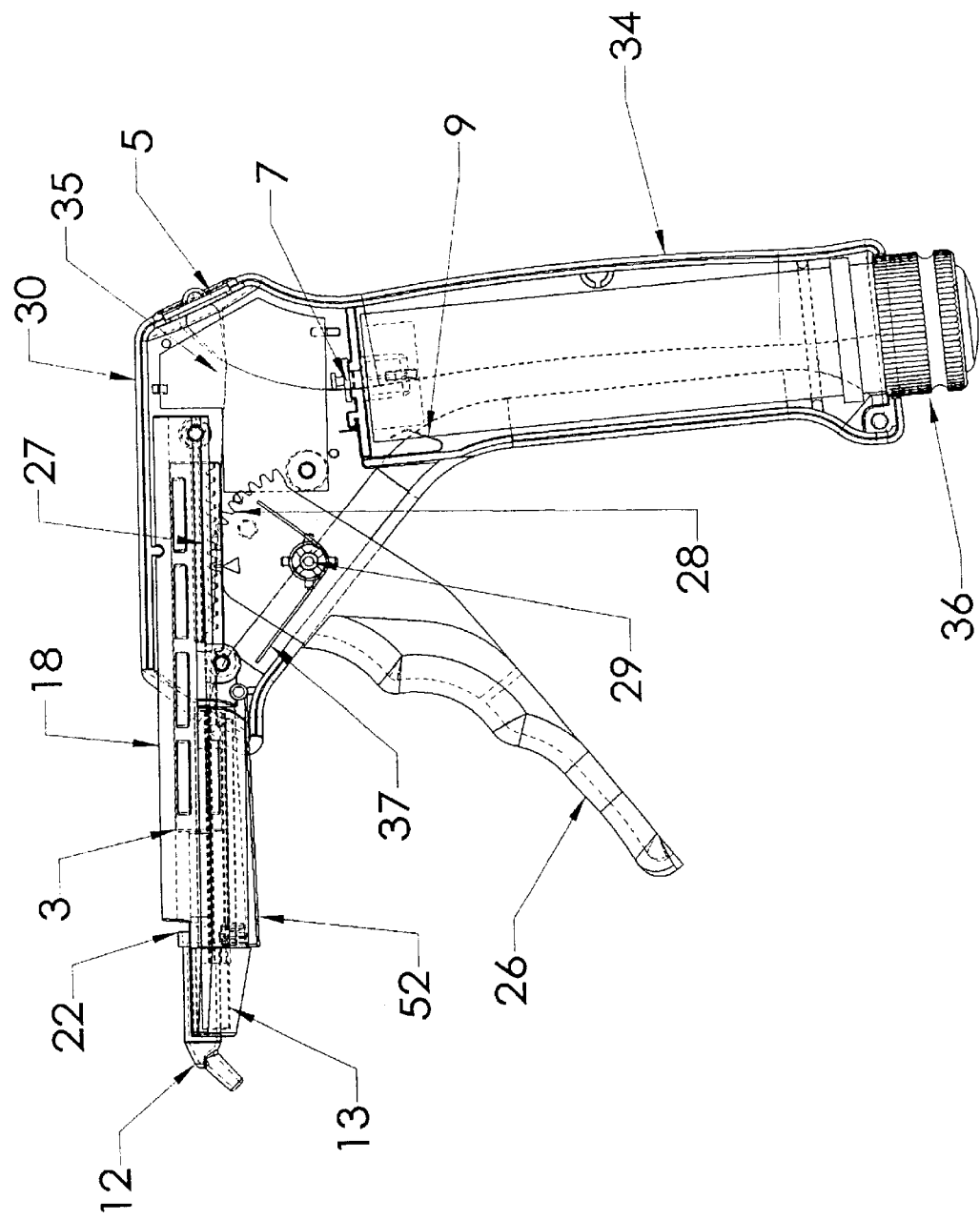
FIG. 3 is a side elevation of the manually operated dispenser of the present invention taken along the lines 3—3 of FIG. 2.
Figure 7:
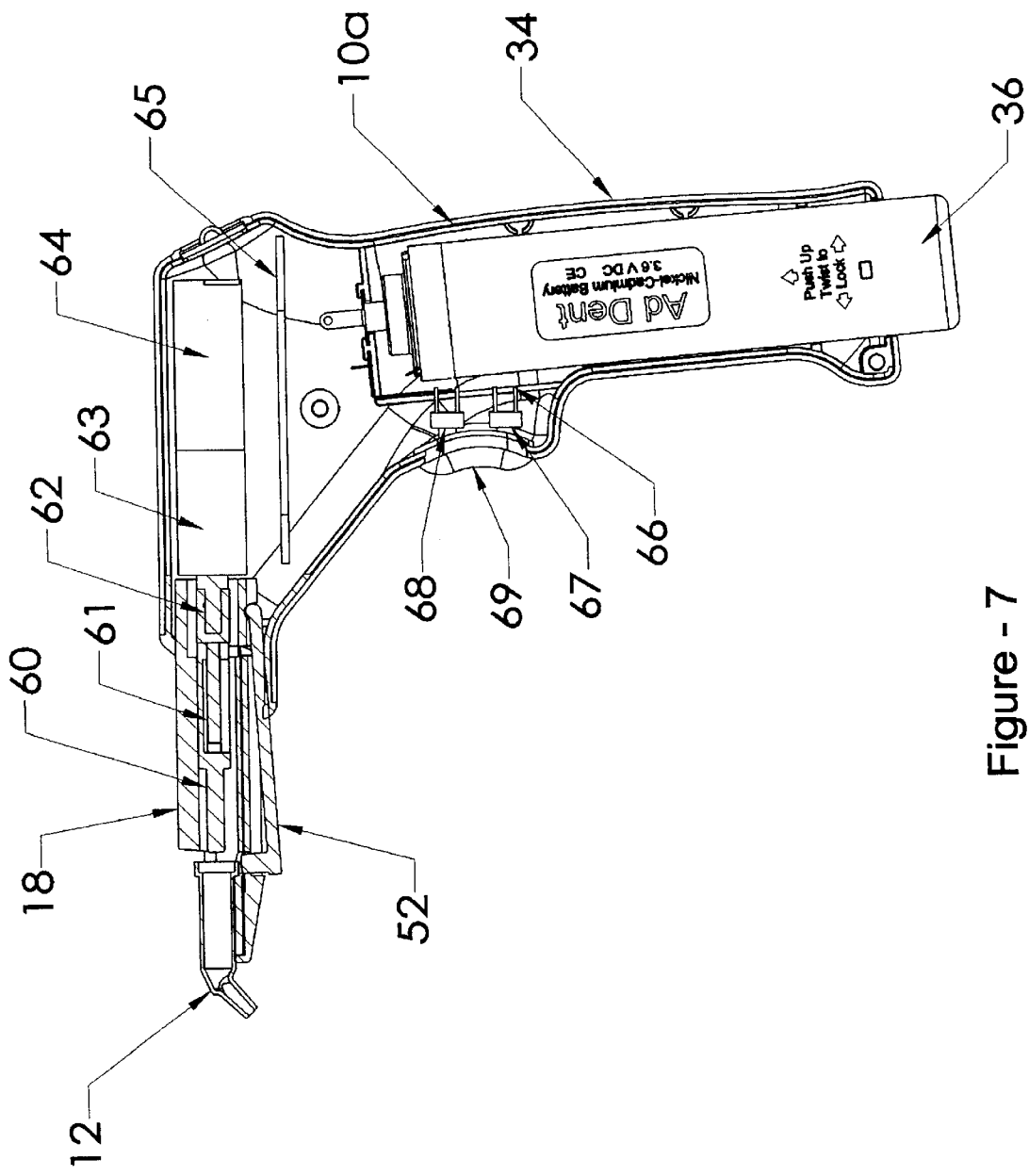
FIG. 7 is another side elevation of the dispenser of the present invention similar to the embodiment of FIG. 3 which employs a motorized dispensing unit instead of a manually operated dispensing unit.
Figure 8:
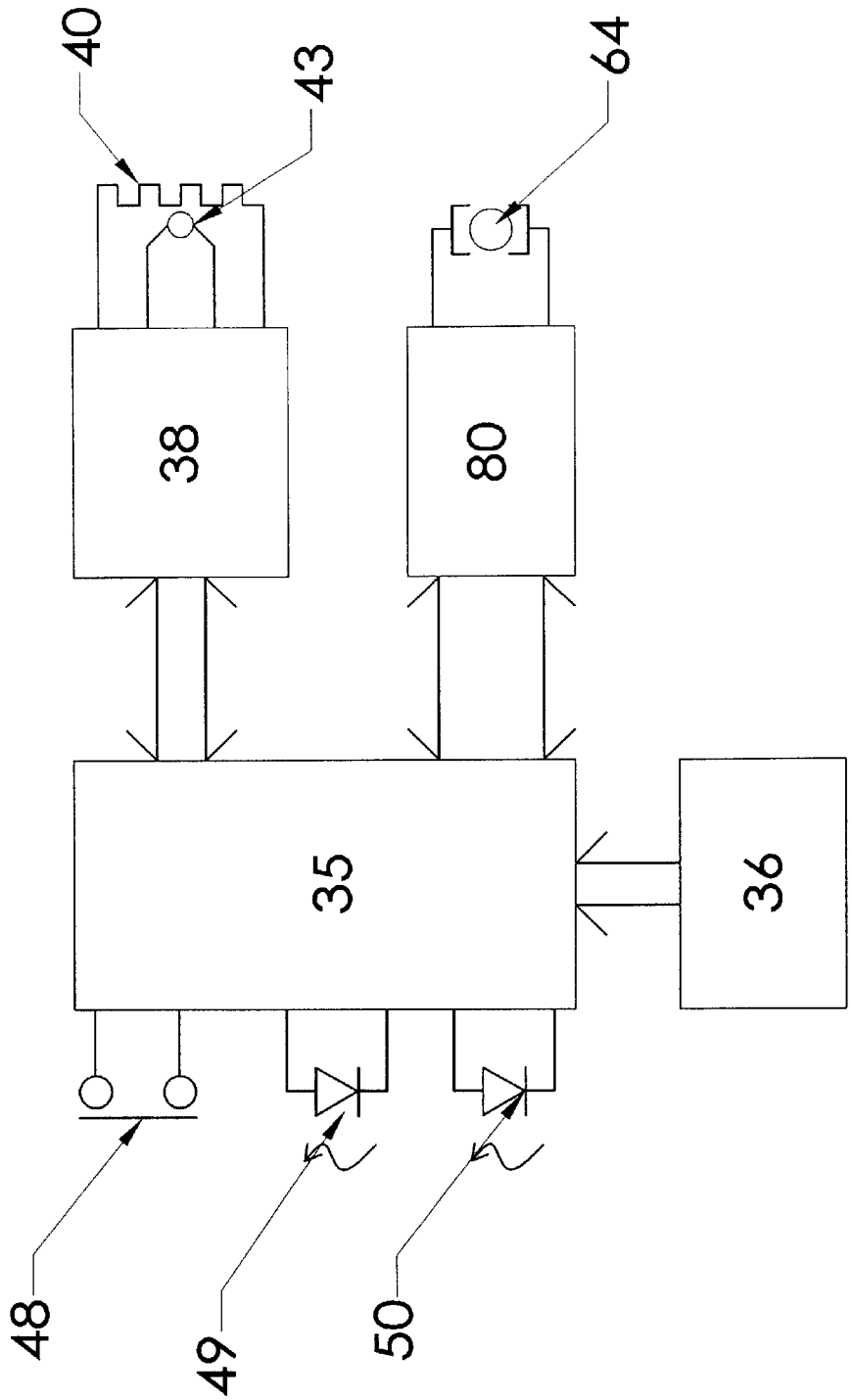
FIG. 8 is a block diagram of the heating control unit for controlling the temperature of the heating unit in FIG. 5 for the motorized dispenser embodiment of FIG. 7.

The dispenser of the present invention is operator controlled by means of a manual mechanism which drives the plunger 24 as described heretofore in connection with FIGS. 3, 4 and 6 or alternatively a motorized assembly and drive unit 80 which drives a plunger 60 as shown in FIGS. 7 and 8 inclusive. The dispenser 10a of FIG. 7 is substantially equivalent to the dispenser 10 of FIGS. 1 and 3 with parts in common identified by the same reference numbers. Accordingly, the housing 30, tubular section 34, battery compartment 36, tubular barrel 18 and open front end cavity design inclusive of a compule holder 13 into which a compule 12 is removably inserted and the ejector arm 52 for manually ejecting a spent compule 12 are identical in the two embodiments. In fact the dispenser 10a is substantially equivalent to the dispenser 10 in all respects except for control of the plunger which is motorized in the dispenser embodiment 10a of FIGS. 7 and 8. In the dispenser 10a of FIG. 7 a motor 64 is employed to control a plunger 60 which is operationally equivalent to plunger 24 but otherwise adapted to be connected to a conventional lead screw 61. The motor 64 is a conventional DC motor which drives the lead screw 61. The lead screw 61 is connected to the drive shaft 62 of the motor 64 preferably through a conventional gearbox 63. The gearbox 63 is a gear reduction assembly having a gear ratio which will cause a significant speed reduction of the drive shaft 62 to a preferred speed range of 30–300 RPM. The reduced speed of the drive shaft 62 causes a substantial increase in output torque which provides for greater control in dispensing dental material from the compule 12.

The lead screw 61 drives the plunger 60 in response to a command signal from the operator under the control of the motor drive unit 80 shown in FIG. 8. The motor drive unit 80 is a microprocessor which may be separate from or an integral part of the microprocessor in control unit 35. The control circuit 35 will instruct the motor drive unit 80 to drive the motor 64 either forward or backward depending upon which of two manual switches 67 or 68 is depressed with e.g. switch 68 controlling forward motion and switch 67 reverse motion. The control unit 35 otherwise provides all of the same functions as described earlier. If the motor 64 approaches stall torque (i.e. when the current increases at a rapid rate) the motor drive unit 80 will sense the end of forward travel. Under this condition the motor direction will be reversed retracting the plunger 60 from contact with the compule 12 to permit the spent compule 12 to be removed. The manual switches 67 and 68 are hard wired to a circuit board 66 which is connected to the circuit board 65 containing all of the circuits in the block diagram of FIG. 8 inclusive of the control unit 35 and the drive unit 80. A protective cover 69 is mounted over the switches 67 and 68 to protect the control switches.

In operation the control unit 35 is designed to ignore operation of the forward switch button 68 until the desired temperature is reached. Once this occurs the control unit 35 will instruct the motor drive unit 80 to drive the motor 64 forward in response to the operator depressing the forward switch 68 and to continue until under operation of the operator which can be continuous or discontinuous until the end of travel is reached. When the end of travel is reached, the control unit 35 will instruct the motor drive unit 80 to reverse the direction of rotation of the motor 64 and return it to a given "home" position.

What is claimed is:

1. A dispenser for heating and extruding dental material from a compule of dental material removably inserted within said dispenser comprising:

an elongated section having a front end and a rear end with said front end having a cavity open to the atmosphere for removably receiving said compule, a plunger mounted for reciprocal movement within the elongated section of said dispenser in alignment with the cavity, means in response to the control of an operator for advancing the plunger into engagement with said compule to express dental material from said compule, a heating unit having a resistive heating element located in the front end of said dispenser below said cavity and upon which said compule is mounted for heating substantially the entire compule in said cavity such that all or substantially all of the material in the compule is heated at one time;

a supply of electrical energy and means for controlling the supply of electrical energy to said heating element in the heating unit.

2. A dispenser for heating and extruding dental material as defined in claim 1 wherein said means for advancing the plunger into engagement with said compule is a motorized assembly.

3. A dispenser for heating and extruding dental material as defined in claim 2 wherein said motorized assembly comprises a motor having a drive shaft and a lead screw coupled to the drive shaft through a gearbox.

4. A dispenser for heating and extruding dental material as defined in claim 3 wherein said gear box has a gear reduction assembly with a gear ratio for causing said drive shaft to rotate at a speed of between 30–300 RPM.

5. A dispenser for heating and extruding dental material as defined in claim 3 further comprising a control circuit, motor drive unit and a manual control under the operation of the operator for generating a command signal to instruct the motor drive unit to operate the motor in one of two directions for controlling forward or backward motion of the lead screw.

6. A dispenser for heating and extruding dental material as defined in claim 5 wherein said manual control includes a push button.

7. A dispenser for heating and extruding dental material as defined in claim 5 wherein said control circuit comprises a microprocessor for driving said motor drive unit to motor forward or backward and an operator interface responsive to said heating unit.

8. A dispenser for heating and extruding dental material as defined in claim 3 wherein said means for controlling the supply of electrical energy is a battery pack removably located in said dispenser.

9. A dispenser for heating and extruding dental material as defined in claim 8 wherein said heating unit further includes a temperature sensing element.

10. A dispenser for heating and extruding dental material as defined in claim 9 wherein said temperature sensing element is a thermocouple.

11. A dispenser for heating and extruding dental material as defined in claim 3 wherein said heating unit is in the form of a flexible sheet liner covering an internal surface of the cavity in contact with the compule.

12. A dispenser for heating and extruding dental material as defined in claim 1 further comprising a manually movable compule ejector arm having a head extending through an opening in the dispenser below said cavity for manually ejecting said compule upon manually depressing the ejector arm to lift the head thereby raising the compule upwardly out from the cavity.

* * * * *